US009976965B2

(12) United States Patent
Seo et al.

(10) Patent No.: US 9,976,965 B2
(45) Date of Patent: May 22, 2018

(54) WELDING FACILITY INSPECTING APPARATUS

(71) Applicant: Kia Motors Corporation, Seoul (KR)

(72) Inventors: Bokdeok Seo, Paju-si (KR); Seongrae Nho, Suwon-si (KR); Jimyeon Song, Cheonan-si (KR)

(73) Assignee: Kia Motors Corporation, Seoul (KR)

( * ) Notice: Subject to any disclaimer, the term of this patent is extended or adjusted under 35 U.S.C. 154(b) by 749 days.

(21) Appl. No.: 14/560,551

(22) Filed: Dec. 4, 2014

(65) Prior Publication Data

US 2015/0177156 A1    Jun. 25, 2015

(30) Foreign Application Priority Data

Dec. 20, 2013    (KR) ........................ 10-2013-0160721

(51) Int. Cl.
| | |
|---|---|
| B23K 11/36 | (2006.01) |
| G01L 1/00 | (2006.01) |
| G01N 21/88 | (2006.01) |
| H04N 5/247 | (2006.01) |
| G01R 19/00 | (2006.01) |

(52) U.S. Cl.
CPC .............. *G01N 21/88* (2013.01); *B23K 11/36* (2013.01); *G01L 1/00* (2013.01); *G01N 21/8806* (2013.01); *G01R 19/0092* (2013.01); *H04N 5/247* (2013.01); *G01N 2201/12* (2013.01)

(58) Field of Classification Search
CPC .......... B23K 11/36; G01L 1/00; G01N 21/88; G01N 21/8806; G01N 2201/12; G01R 19/0092; H04N 5/247

USPC .......................................................... 348/90
See application file for complete search history.

(56) References Cited

U.S. PATENT DOCUMENTS

| | | | |
|---|---|---|---|
| 2009/0173726 A1* | 7/2009 | Davidson ............. | B23K 9/0956 219/130.01 |
| 2017/0043851 A1* | 2/2017 | Kimura ................... | B63C 11/52 |

FOREIGN PATENT DOCUMENTS

| | | | |
|---|---|---|---|
| CN | 102240838 A | | 11/2011 |
| CN | 102642075 A | | 8/2012 |
| EP | 1 964 639 A1 | | 9/2008 |
| JP | 2-34286 A | | 2/1990 |
| JP | 4-65608 A | | 3/1992 |
| JP | 8-271236 A | | 10/1996 |
| JP | 2009-285725 A | | 12/2009 |
| JP | 2010051997 | * | 3/2010 |
| JP | 4971272 B2 | | 4/2012 |

(Continued)

*Primary Examiner* — Jamie Atala
*Assistant Examiner* — James Boylan
(74) *Attorney, Agent, or Firm* — Morgan, Lewis & Bockius LLP (57) ABSTRACT

A welding facility inspecting apparatus may include a base apparatus that has a space in the interior thereof and surrounds the space in a horizontal direction, a first extension apparatus, a second extension apparatus, a first camera that is attached to the base apparatus, a second camera that is attached to the base apparatus at a same height as the first camera, a third camera that is attached to the first extension apparatus, a fourth camera that is attached to the second extension apparatus, and a measuring apparatus that is attached to the base apparatus in such a way that the measuring apparatus is disposed in the inner space of the base apparatus and that is configured to measure welding force and welding current of a welding gun.

18 Claims, 5 Drawing Sheets

(56) References Cited

FOREIGN PATENT DOCUMENTS

| JP | 2012-187588 A | 10/2012 |
|---|---|---|
| KR | 10-2012-0050411 A | 5/2012 |
| KR | 10-1258170 B1 | 5/2013 |
| WO | WO 2013/114506 A1 | 8/2013 |

\* cited by examiner

WELDING FACILITY INSPECTING APPARATUS

CROSS-REFERENCE TO RELATED APPLICATION

The present application claims priority to Korean Patent Application No. 10-2013-0160721 filed Dec. 20, 2013, the entire contents of which is incorporated herein for all purposes by this reference.

BACKGROUND OF THE INVENTION

Field of the Invention

The present invention relates to a welding facility inspecting apparatus, and particularly to a welding facility inspecting apparatus that is configured to integratively inspect a variety of welding facility functions and states.

Description of Related Art

Generally speaking, welding means bonding a metallic material based on a direct atom coupling between two different solid materials.

Particularly, most of the portions of a vehicle body are bonded by a welding. That is, the welding facility is a key facility in a vehicle body manufacture of a vehicle. Further, an electric welding is mainly used when welding a vehicle body. Meanwhile, if a defect is found in the welding of a vehicle body, the safety of a driver significantly deteriorates.

The defects in the welding facility may directly lead to the defects of the welding. Therefore, it is very important to inspect the welding facility before the manufacture of the vehicle body of a vehicle. Particularly, during a welding facility inspection, it needs to basically inspect the functions and states of a welding gun of a welding facility. The inspection of the welding gun consists of a welding force inspection of a welding gun, a welding current inspection, a rectilinear propagation performance inspection, an abrasion loss inspection and a polishing condition inspection.

According to the related art, the welding force inspection and the welding current inspection of the welding gun have been performed in such a way to manually measure the welding force and the welding current of a welding gun using certain measuring equipment and to inspect whether the welding force and the welding current of the welding gun satisfy the previously set values. Further, the rectilinear propagation performance inspection of the welding gun has been performed by visually inspecting the rectilinear propagation performance of a welding gun, and the abrasion loss inspection of the welding gun has been performed in such a way to adjust the data with respect to the abrasion loss when a problem occurs due to an error in the actual abrasion loss and data. In addition, the polishing condition inspection of a welding gun has been performed in such a way to reflect light on the surface of a tip of the welding gun and to check the quantity of the reflecting light.

However, each of the above-described conventional inspections for the welding gun has been separately performed, which results in complicated procedures. Further, the manual and visual inspections require a high concentration for an inspection worker, and the accuracy of the inspection may deteriorate. In addition, any measure taken after the occurrence of a problem may not be effective to prevent any defects prior to welding.

The information disclosed in this Background of the Invention section is only for enhancement of understanding of the general background of the invention and should not be taken as an acknowledgement or any form of suggestion that this information forms the prior art already known to a person skilled in the art.

BRIEF SUMMARY

Various aspects of the present invention are directed to providing a welding facility inspecting apparatus that is configured to integratively inspect a variety of welding gun functions and states.

Further, various aspects of the present invention are directed to providing a welding facility inspecting apparatus that is configured to accurately check any defect in a welding gun and to previously prevent any defect in a welding.

According to various aspects of the present invention, a welding facility inspection apparatus may include a base apparatus that has a space in the interior thereof and surrounds the space in a horizontal direction, a first extension apparatus that protrudes and extends upward from the base apparatus, a second extension apparatus that protrudes and extends downward from the base apparatus, a first camera that is attached to the base apparatus and takes a picture of the inner space of the base apparatus in a horizontal direction, a second camera that is attached to the base apparatus at a same height as the first camera and takes a picture of the inner space of the base apparatus in a horizontal direction and that has a photographing direction that an extension line thereof is perpendicularly crossed with an extension line of a photographing direction of the first camera, a third camera that is attached to the first extension apparatus and takes a picture of the inner space of the base apparatus from an upper side of the inner space of the base apparatus, a fourth camera that is attached to the second extension apparatus and takes a picture of an inner space of the base apparatus from a lower side of the inner space of the base apparatus, and a measuring apparatus that is attached to the base apparatus in such a way that the measuring apparatus is disposed in the inner space of the base apparatus and that is configured to measure welding force and welding current of a welding gun, in which the welding gun may be disposed in the inner space of the base apparatus, and the first, second, third and fourth cameras each may be configured to selectively take a picture of the welding gun.

The welding gun may be provided as a pair vertically with respect to the base apparatus, and the pair of welding guns may be disposed in such a way that welding tips of each of the welding guns face each other, and in a state that the base apparatus is disposed so that the welding gun can be disposed where the photographing direction of the first camera and the photographing direction of the second camera cross each other, the first and second cameras may be configured to take a picture of the welding gun.

Rectilinear propagation performance and the abrasion loss of the welding gun may be inspected using images taken by the first and second cameras.

The welding gun may be provided as a pair vertically with respect to the base apparatus, and the pair of welding guns may be disposed so that welding tips of each of the welding guns face each other, and in a state that the pair of welding guns are spaced by a predetermined distance, the third camera may be configured to take a picture of a welding tip of a lower positioned welding gun between the pair of welding guns and the fourth camera may be configured to take a picture of a welding tip of an upper positioned welding gun between the pair of welding guns.

The base apparatus may be disposed so that the welding gun is disposed where the photographing direction of the first camera and the photographing direction of the second camera cross each other.

A polishing condition of the welding gun may be inspected using images taken by the third and fourth cameras.

The welding facility inspecting apparatus may further include a computer that is configured to control operations of the first, second, third and fourth cameras and the measuring apparatus and to store photographing and inspection data.

The computer may be configured to calculate a correction value that is based on the inspection data.

According to various aspects of the present invention, a welding facility inspecting apparatus may include a frame that has a space in the interior thereof and has a horizontal circumference of the space and has a portion that protrudes upward and downward, a first camera that is attached to the circumference of the frame and takes a picture of an inner space of the frame in a horizontal direction, a second camera that is attached to the circumference of the frame at a same height as the first camera and takes a picture of the inner space of the frame in the horizontal direction and that has a photographing direction that an extension line thereof is perpendicularly crossed with an extension line of a photographing direction of the first camera, a third camera that is attached to the portion protruding in the upward direction of the frame and takes a picture of the inner space of the frame from an upper side of the inner space of the frame, a fourth camera that is attached to the portion protruding in the downward direction of the frame and takes a picture of the inner space of the frame from a lower side of the inner space of the frame, a measuring apparatus that is attached to the circumference of the frame so that the measuring apparatus is disposed in the inner space of the frame and that is configured to measure a welding force and a welding current of a welding gun, a robot that is connected to the frame and moves so that the frame is disposed at a desired position, a power supply apparatus that is configured to supply electric power to the robot so that the robot operates, and a carrier that carries the robot and the power supply apparatus and is configured to carry the robot and the power supply apparatus to a desired position, in which the welding gun may be disposed in the inner space of the frame, and the first, second, third and fourth cameras each may be configured to selectively take a picture of the welding gun.

The welding facility inspecting apparatus may further includes a computer that is configured to control operations of the first, second, third and fourth cameras and the measuring apparatus and to store photographing and inspection data, and a robot controller that is configured to control the robot.

The computer may be configured to calculate a correction value that is based on the inspection data.

The computer may be configured to transmit the inspection data and the data of the calculated correction value of the welding gun using wireless communication to a server.

The inspection result and the calculated correction value of the welding gun may be confirmed on the personal computer (PC) connected to the server.

The welding gun may be provided as a pair vertically positioned with respect to a circumference of the frame, and the pair welding guns may be disposed in such a way that the welding tips of each of the welding guns face each other, and in a state that the frame is disposed so that the welding gun is disposed where the photographing direction of the first camera crosses the photographing direction of the second camera, the first and second cameras may be configured to take a picture of the welding gun.

Rectilinear propagation performance and abrasion loss of the welding gun may be inspected using images taken by the first and second cameras.

The welding gun may be provided as a pair vertically positioned with respect to a circumference of the frame, and the pair of welding guns may be disposed so that welding tips of each of the welding guns face each other, and in a state that the pair of welding guns are spaced apart by a predetermined distance, the third camera may be configured to take a picture of a welding tip of a lower positioned welding gun between the pair of welding guns, and the fourth camera may be configured to take a picture of a welding tip of an upper positioned welding gun between the pair of welding guns.

The frame may be disposed so that the welding gun is disposed where the photographing direction of the first camera crosses the photographing direction of the second camera.

A polishing condition of the welding gun may be inspected using images taken by the third and fourth cameras.

As described above, according to various aspects of the present invention, a variety of functions and states of the welding gun can be integratively inspected, so the amount of the time for a welding facility inspection can be reduced.

Further, since the manual and visual inspections of the welding gun can be omitted, it is possible to prevent any inconveniences to workers during the inspection.

In addition, since the function and states of the welding gun are inspected using the cameras and computer, an accurate inspection is possible, and any defects in the welding can be found.

The methods and apparatuses of the present invention have other features and advantages which will be apparent from or are set forth in more detail in the accompanying drawings, which are incorporated herein, and the following Detailed Description, which together serve to explain certain principles of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Figure 1:
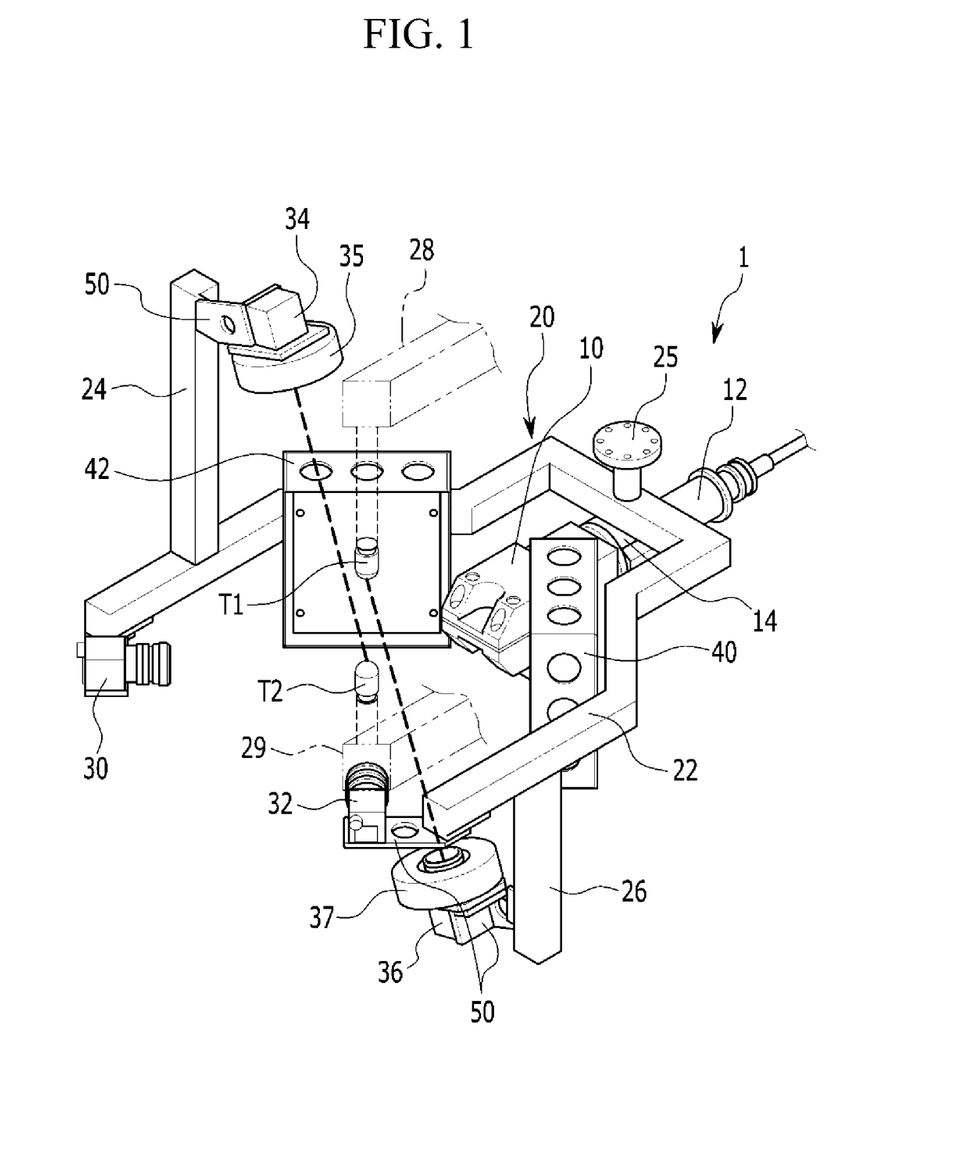
FIG. 1 is a construction view illustrating a state of when an exemplary welding facility inspecting apparatus according to the present invention is inspecting a polishing condition of a welding gun.
Figure 2:
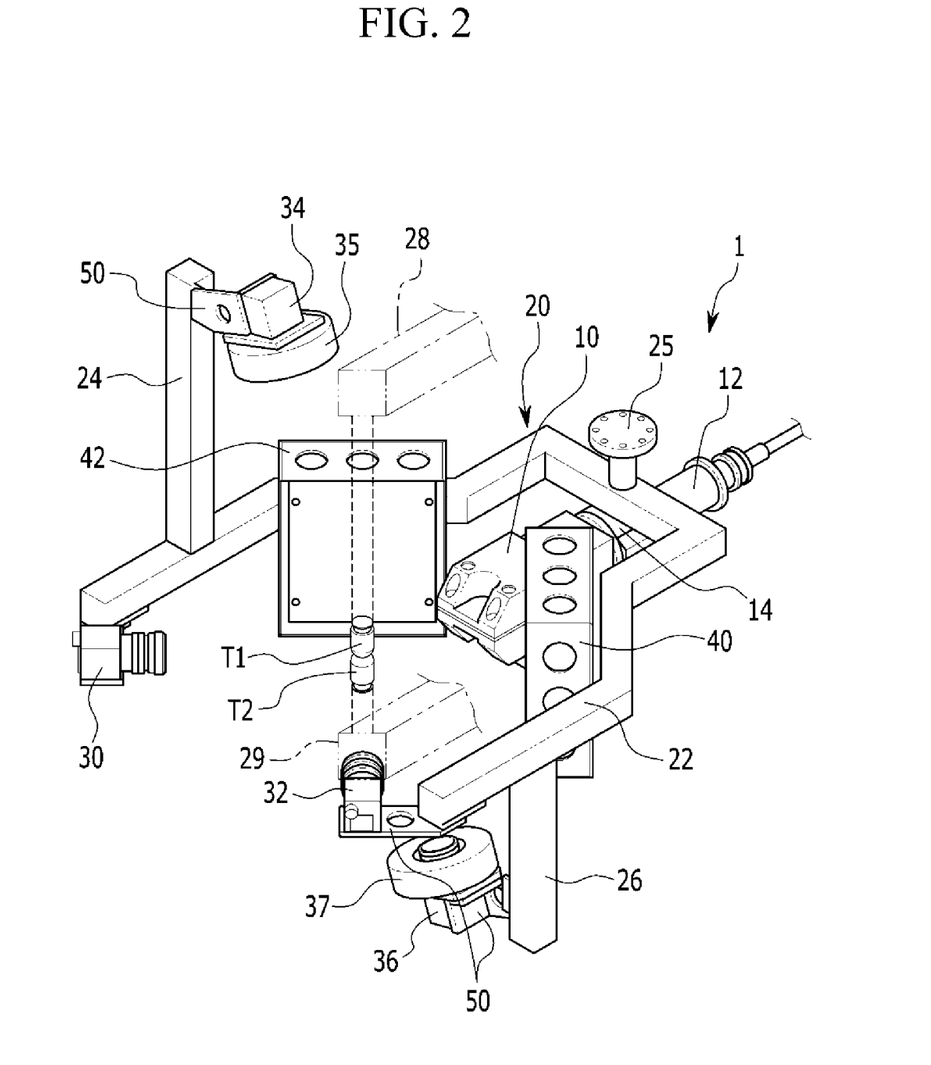
FIG. 2 is a schematic construction diagram illustrating a state of when the exemplary welding facility inspecting apparatus according to the present invention inspects a rectilinear propagation performance and an abrasion loss of a welding gun.
Figure 3:
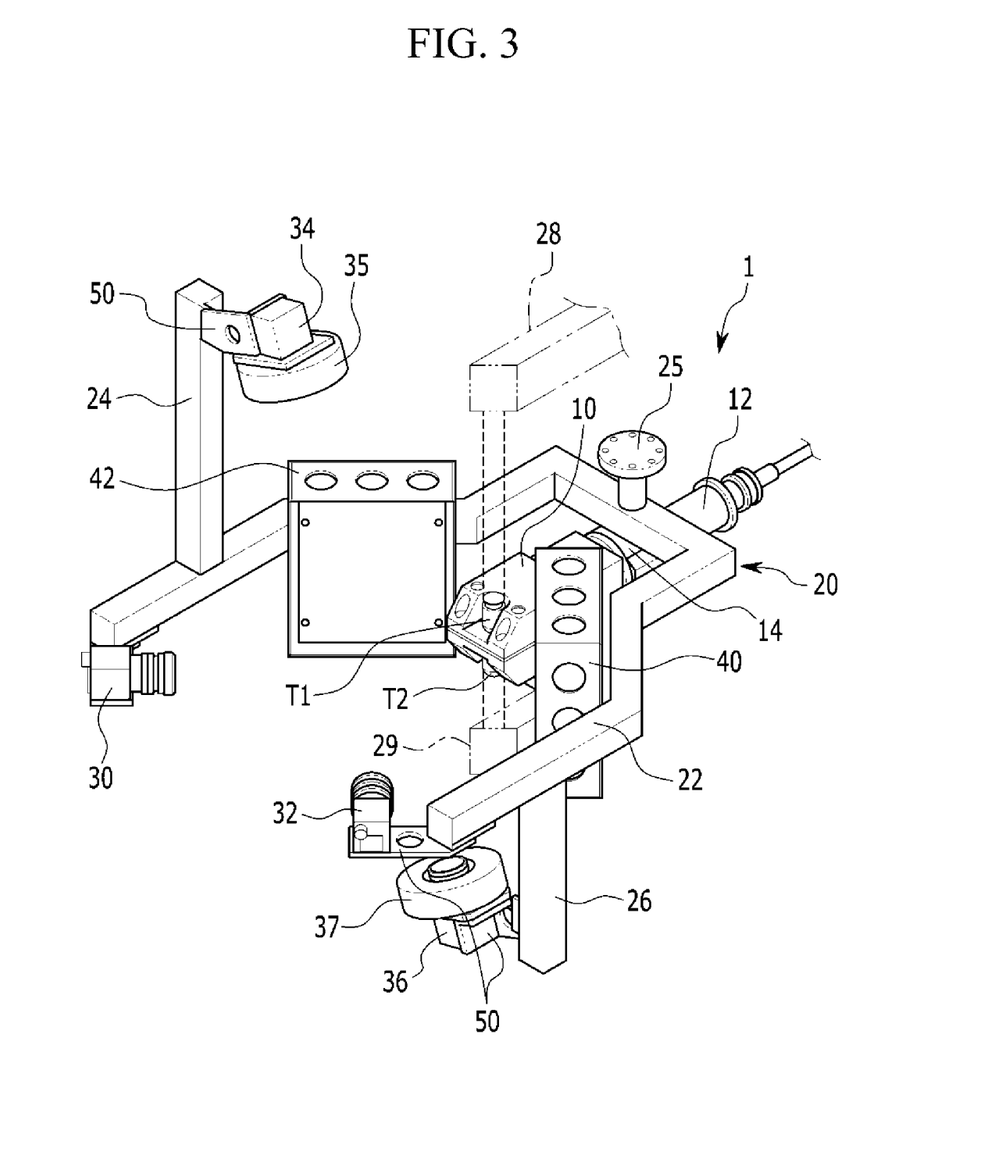
FIG. 3 is a schematic construction diagram illustrating a state of when the exemplary welding facility inspecting apparatus according to the present invention inspects welding current and welding force of a welding gun.

FIG. 1 is a construction view illustrating a state of when a welding facility inspecting apparatus according to various embodiments of the present invention is inspecting a polishing condition of a welding gun, FIG. 2 is a schematic construction diagram illustrating a state of when the welding facility inspecting apparatus according to various embodiments of the present invention inspects a rectilinear propagation performance and an abrasion loss of a welding gun, and FIG. 3 is a schematic construction diagram illustrating a state of when the welding facility inspecting apparatus according to various embodiments of the present invention inspects welding current and welding force of a welding gun.

As illustrated in FIG. 1, FIG. 2 and FIG. 3, the welding facility inspecting apparatus 1 according to various embodiments of the present invention includes a frame 20, a measuring unit 10, cameras 30, 32, 34 and 36 and reflection plates 40 and 42.

The frame 20 is a support on which the measuring unit 10, the cameras 30, 32, 34 and 36 and the reflection plates 40 and 42 are mounted. Further, the measuring unit 10, the cameras 30, 32, 34 and 36 and the reflection plates 40 and 42 are mounted on the frame 20 in accordance with a design choice by a person having an ordinary skill in the art.

The frame 20 includes a base unit 22, a first extension unit 24, a second extension unit 26 and an engaging member 25.

The base unit 22 is installed in a U-shape such that the welding guns 28 and 29 that will be inspected are disposed in its inner space, and the measuring unit 10, the cameras 30, 32, 34 and 36 and the reflection plates 40 and 42 are disposed on its circumferential surface. Further, the U-shaped open portion of the base unit 22 allows the frame 20 to move smoothly so that the welding guns 28 and 29 can be disposed in the inner space of the base unit 22. In addition, the U-shape of the base unit 22 is horizontally disposed.

The first extension unit 24 protrudes upward from the base unit 22 and extends, and the second extension unit 26 protrudes downward from the base unit 22 and extends.

The engaging member 25 enables the measuring unit 10 to be coupled to a part of the surrounding portions of the base unit 22. Here, the engaging member 25 may be a bolt type that passes through a part of the base unit 22 and to attach with the measuring unit 10.

The measuring unit 10 is a device to measure welding force and welding current of the welding guns 28 and 29. Further, the measuring unit 10 is coupled to a part of the base unit 22 so that the measuring unit 10 can be disposed in an inner space of the base unit 22. In addition, the measuring unit 10 is connected to an electric power supply cable 12 so as to receive electric power from the electric power source.

The cameras 30, 32, 34 and 36 consist of first, second, third and fourth cameras 30, 32, 34 and 36.

The first camera 30 is mounted on the base unit 22 of the frame 20. Further, the first camera 30 is configured to take in a horizontal direction a picture of an inner space of the base unit 22.

The second camera 32 is mounted on the base unit 22 of the frame 20. Further, the second camera 32 is configured to take in a horizontal direction a picture of an inner space of the base unit 22. In addition, the first camera 30 and the second camera 32 are disposed so that the photographing angle can be 90° at the same heights.

The third camera 34 is mounted on the first extension unit 24 of the frame 20. Further, the third camera 34 is disposed to take a picture of an inner space of the base unit 22 from the upper side of the inner space of the base unit 22.

The fourth camera 36 is mounted on the second extension unit 26 of the frame 20. Further, the fourth camera 36 is disposed to take a picture of an inner space of the base unit 22 from the lower side of the inner space of the base unit 22. In addition, the cameras 30, 32, 34 and 36 may be mounted on a bracket 50 that is fixed to the frame 20.

The reflection plates 40 and 42 consist of a first reflection plate 40 and a second reflection plate 42.

Both the first reflection plate 40 and the second reflection plate 42 are mounted on the base unit 22 of the frame 20. In addition, the first reflection plate 40 is disposed facing the first camera 30 and the second reflection plate 42 is disposed facing the second camera 32. Since the reflection plates 40 and 42 that help the photographing of the cameras 30 and 32 using the reflections of light are obvious to a person having an ordinary skill in the art, the descriptions thereof will be omitted.

Meanwhile, the welding guns 28 and 29 consist of a first welding gun 28 and a second welding gun. Further, the first welding gun 28 and the second welding gun 29 are disposed to weld at both sides of a welding object. That is, the first welding gun 28 and the second welding gun 29 are disposed facing each other. In addition, the first welding gun 28 and the second welding gun 29 are disposed vertically with respect to the base unit 22, and the first welding gun 28 is disposed at the upper portion, and the second welding gun 29 is disposed at the lower portion. Furthermore, at an end portion of the first welding gun 28 facing the second welding gun 29 is installed a first welding tip "T1", and at an end portion of the second welding gun 29 facing the first welding gun 28 is installed a second welding tip "T2". Since the functions of the welding guns 28 and 29 and the welding tips "T1" and "T2" are obvious to a person having an ordinary skill in the art, the detailed descriptions thereof will be omitted.

As illustrated in FIG. 1, in order to inspect the polishing condition of the first and second welding guns 28 and 29, the frame 20 is disposed so that the first and second welding guns 28 and 29 can be disposed in the inner space of the base unit 22. Further, the first welding tip "T1" of the first welding gun 28 is spaced apart by a predetermined distance from the second welding tip "T2" of the second welding gun 29.

In a state that the first welding tip "T1" and the second welding tip "T2" are spaced apart, the third camera 34 takes a picture of the second welding tip "T2" and the fourth camera 36 takes a picture of the first welding tip "T1". In this case, lighting units 35 and 37 are disposed in the third and fourth cameras 34 and 36, respectively, in order to help the third and fourth cameras 34 and 36 take pictures. That is, the lighting unit 35 of the third camera 34 irradiates light on the second welding tip "T2" and the lighting unit 37 of the fourth camera 36 irradiates light on the first welding tip "T1".

The polishing condition of the second welding tip "T2" can be inspected using the images taken by the third camera 34. Further, the polishing condition of the first welding tip "T1" can be inspected using the images taken by the fourth camera 36. That is, the third camera 34 and the fourth camera 36 take pictures of the surface of the second welding tip "T2" and the surface of the first welding tip "T1", respectively, and the areas of the impurities attached to the surface of the second welding tip "T2" and the surface of the first welding tip "T1" can be inspected using the images of the surface of the second welding tip "T2" and the surface of the first welding tip "T1".

As illustrated in FIG. 2, in order to inspect a rectilinear propagation performance and an abrasion loss of the first and second welding guns 28 and 29, the frame 20 is disposed so that the first and second welding guns 28 and 29 can be disposed in the inner space of the base unit 22

Further, the approaching of the first welding tip "T1" of the first welding gun 28 and the second welding tip "T2" of the second welding gun 29 is determined based on the vertical movement values of the first welding gun 28 and the second welding gun 29 set based on the previously set distance between the first welding tip "T1" and the second welding tip "T2". In addition, the first and second welding guns 28 and 29 are positioned where the photographing direction of the first camera 30 and the photographing direction of the second camera 32 cross each other based on the arrangement of the frame 20 so that the first and second cameras 30 and 32 can simultaneously take pictures of both the approaching first and second welding tips "T1" and "T2".

The rectilinear propagation performance and the abrasion loss of the first and second welding tips "T1" and "T2" can be inspected using the images simultaneously taken by the first and second cameras 30 and 32.

The inspections for the rectilinear propagation performances of the first and second welding tips "T1" and "T2" are directed to inspecting whether the first and second welding tips "T1" and "T2" can be accurately folded so as to weld the same portions. That is, the inspection for the rectilinear propagation performance of the first and second welding tips "T1" and "T2" may be directed to inspecting whether the centers of the first and second welding tips "T1" and "T2" are positioned on the vertical line. In this case, since the first and second cameras 30 and 32 are disposed at the angle of 90°, the first and second welding tips "T1" and "T2" can be accurately folded once the rectilinear propagation performances of the first and second welding tips "T1" and "T2" are compensated in the image taken by the first camera 30 and in the image taken by the second camera 32.

The inspection for the abrasion losses of the first and second welding tips "T1" and "T2" is directed to measuring the distance between the first welding tip "T1" and the second welding tip "T2" using the images taken by the first and second cameras 30 and 32 in a state where the first welding tip "T1" and the second welding tip "T2" are close to each other based on the previously set vertical movement values of the first welding gun 28 and the second welding gun 29. Here, if the measured distance between the first welding tip "T1" and the second welding tip "T2" is greater than the distance between the first welding tip "T1" and the second welding tip "T2" which was previously set before the abrasions of the first welding tip "T1" and the second welding tip "T2" due to the abrasions of the first and second welding tips "T1" and "T2", the vertical movement values of the first and second welding guns 28 and 29 can be reset so that the distance between the first welding tip "T1" and the second welding tip "T2" becomes the previously set distance.

Meanwhile, while the polishing condition, the rectilinear propagation performance and the abrasion loss of the first and second welding guns 28 and 29 are being inspected so as to minimize the movement of the frame 20, the frame 20 can be disposed identically so that the first and second welding guns 28 and 29 can be positioned where the photographing direction of the first camera 30 crosses the photographing direction of the second camera 32.

As illustrated in FIG. 3, the frame 20 is disposed so that the first and second welding guns 28 and 29 can be disposed in the inner space of the base unit 22 so as to inspect the welding current and the welding force of the first and second welding guns 28 and 29. Further, as the frame 20 is disposed in such a way, the first welding gun 28 is disposed above the measuring unit 10, and the second welding gun 29 is disposed below the measuring unit 10. In addition, the first welding tip "T1" of the first welding gun 28 and the second welding tip "T2" of the second welding gun 29 press the measuring unit 10 from both upper and lower sides as the first welding gun 28 and the second welding gun 29 move vertically. In this case, the measuring unit 10 measures the welding currents and the welding force of the first and second welding guns 28 and 29 and compares the measured welding current and welding force with set values, respectively.

Figure 4:
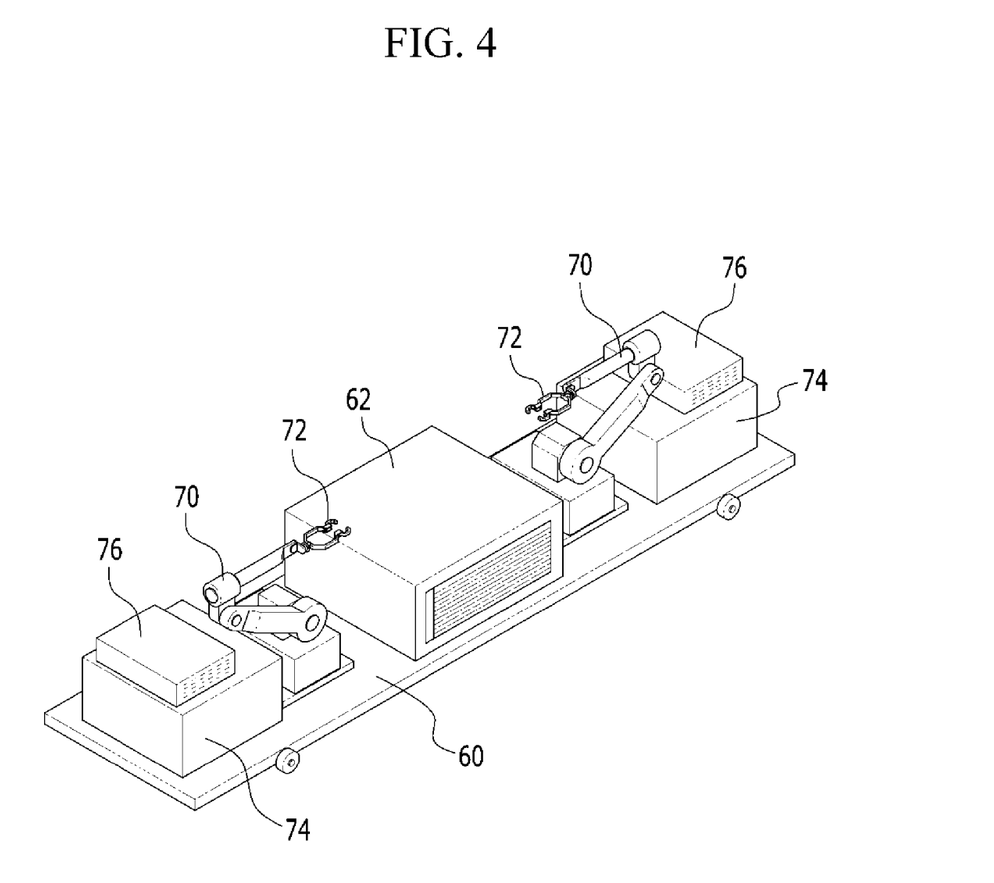
FIG. 4 is a perspective view illustrating a carrier according to the present invention.

FIG. 4 is a perspective view illustrating a carrier according to various embodiments of the present invention.

As illustrated in FIG. 4, a robot 70, a power supply unit 62, a robot controller 74 and a computer 76 are loaded in or mounted on the carrier 60 according to various embodiments of the present invention.

The carrier 60 serves to carry the robot 70, the power supply unit 62, the robot controller 74 and the computer 76 to a place where the welding facility to be inspected is placed.

The robot 70 is a movable robot arm that is configured to dispose the welding facility inspecting apparatus 1 as illustrated in FIG. 1, FIG. 2 and FIG. 3. Further, at an end of the robot 70 is provided a hanger 72 on which the frame 20 is supported. Meanwhile, the hanger 72 may be a part of the frame 20 itself. That is, the welding facility inspecting apparatus 1 may be integral with the robot 70 or may be provided (refer to FIG. 5).

The robot controller 74 is a device for controlling the robot 70.

The computer 76 is configured to control the operations of the measuring unit 10 and the cameras 30, 32 34 and 36. Further, the computer 76 stores the inspection data of the welding guns 28 and 29 and calculates correction values.

The power supply unit 62 serves to supply electric power to the robot 70 so that the robot 70 can work. Further, the power supply unit 62 may be an uninterruptable power supply (UPS) that is configured to prevent a voltage disconnection or a sudden voltage rise or drop in an electric circuit.

Figure 5:
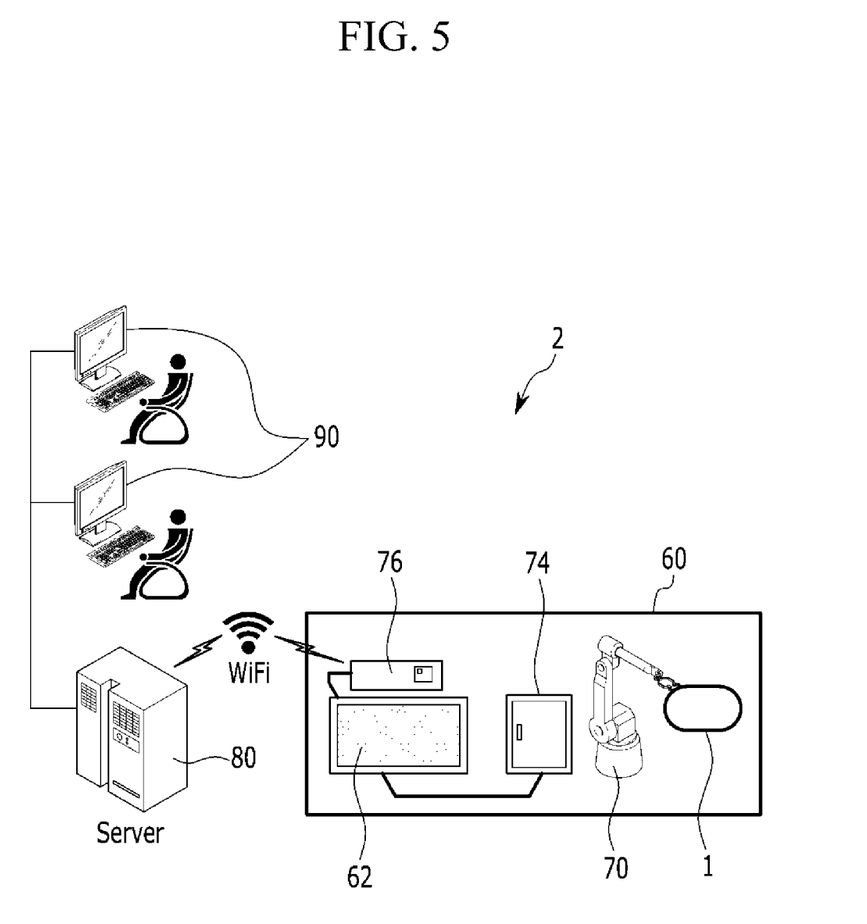
FIG. 5 is a schematic view illustrating a data transmission apparatus that is configured to transmit data of the exemplary welding facility inspecting apparatus according to the present invention.

FIG. 5 is a schematic view illustrating a data transmission unit that is configured to transmit the data of a welding facility inspecting apparatus according to various embodiments of the present invention.

As illustrated in FIG. 5, the data transmission unit 2 according to various embodiments of the present invention includes a server 80 and a personal computer (PC) 90.

The computer 76 is configured to transmit to the server 80 the inspection result data and the calculated correction value data of the welding guns 28 and 29 through wireless communication such as a wireless fidelity (WiFi). Therefore, the worker can confirm the inspection result and the calculated correction values of the welding guns 28 and 29 on the PC 90 connected to the server 80.

According to the various embodiments of the present invention, the various function and states of the welding gun 28 can be inspected in an integrative way, thus decreasing the time for welding facility inspections. Further, since the manual or visual inspections of the welding gun 28 can be omitted, any complicated procedures of the inspection worker need not to be performed by the workers. In addition, since the functions and states of the welding gun 28 can be inspected using the cameras 30, 32, 34 and 36 and the computer 76, an accurate inspection is possible, and any possible defects in the welding can be previously prevented.

For convenience in explanation and accurate definition in the appended claims, the terms "upper", "lower", "inner" and "outer" are used to describe features of the exemplary embodiments with reference to the positions of such features as displayed in the figures.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A welding facility inspecting apparatus, comprising:
    a base member that has a space in the interior thereof and surrounds the space in a horizontal direction;
    a first member that protrudes and extends upward from the base member;
    a second member that protrudes and extends downward from the base member;
    a first camera that is attached to the base member and takes a picture of the inner space of the base member in a horizontal direction;
    a second camera that is attached to the base member s at a same height as the first camera and takes a picture of the inner space of the base member in the horizontal direction and that has a photographing direction that an extension line thereof is perpendicularly crossed with an extension line of a photographing direction of the first camera;
    a third camera that is attached to the first member and takes a picture of the inner space of the base member s from an upper side of the inner space of the base member;
    a fourth camera that is attached to the second member so and takes a picture of the inner space of the base member from a lower side of the inner space of the base member; and
    a measuring apparatus that is attached to the base member in such a way that the measuring apparatus is disposed in the inner space of the base member and that is configured to measure welding force and welding current of a welding gun,
    wherein
    the welding gun is disposed in the inner space of the base member, and the first, second, third and fourth cameras each are configured to selectively take a picture of the welding gun.

2. The apparatus of claim 1, wherein:
    the welding gun is provided as a pair vertically positioned with respect to the base member, and the pair of welding guns are disposed in such a way that welding tips of each of the welding guns face each other, and
    in a state that the base member is disposed so that the welding gun is disposed where the photographing direction of the first camera and the photographing direction of the second camera cross each other, the first and second cameras are configured to take a picture of the welding gun.

3. The apparatus of claim 2, wherein rectilinear propagation performance and abrasion loss of the welding gun are inspected using images taken by the first and second cameras.

4. The apparatus of claim 1, wherein:
    the welding gun is provided as a pair vertically positioned with respect to the base member, and the pair of welding guns are disposed so that welding tips of each of the welding guns face each other, and
    in a state that the pair of welding guns are spaced apart from each other, the third camera is configured to take a picture of a welding tip of a lower positioned welding gun between the pair of welding guns and the fourth camera is configured to take a picture of a welding tip of an upper positioned welding gun between the pair of welding guns.

5. The apparatus of claim 4, wherein:
    the base member is disposed so that the welding gun is disposed where the photographing direction of the first camera and the photographing direction of the second camera cross each other.

6. The apparatus of claim 4, wherein a polishing condition of the welding gun is inspected using images taken by the third and fourth cameras.

7. The apparatus of claim 1, further comprising:
    a computer that is configured to control operations of the first, second, third and fourth cameras and the measuring apparatus and to store photographing and inspection data.

8. The apparatus of claim 7, wherein the computer is configured to calculate a correction value that is based on the inspection data.

9. A welding facility inspecting apparatus, comprising:
    a frame that has a space in the interior thereof and has a horizontal circumferential of the space and has a portion that protrudes upward and downward;
    a first camera that is attached to the circumference of the frame and takes a picture of an inner space of the frame in a horizontal direction;
    a second camera that is attached to the circumference of the frame at a same height as the first camera and takes a picture of the inner space of the frame in the horizontal direction and that has a photographing direction that an extension line thereof is perpendicularly crossed with an extension line of a photographing direction of the first camera;

a third camera that is attached to the portion protruding in the upward direction of the frame and takes a picture of the inner space of the frame from an upper side of the inner space of the frame;

a fourth camera that is attached to the portion protruding in the downward direction of the frame and takes a picture of the inner space of the frame from a lower side of the inner space of the frame;

a measuring apparatus that is attached to the circumference of the frame so that the measuring apparatus is disposed in the inner space of the frame and that is configured to measure a welding force and a welding current of a welding gun;

a robot that is connected to the frame and moves so that the frame is disposed at a desired position;

a power supply apparatus that is configured to supply electric power to the robot so that the robot operates; and a carrier that carries the robot and the power supply apparatus and is configured to carry the robot and the power supply apparatus to a desired position, wherein the welding gun is disposed in the inner space of the frame, and the first, second, third and fourth cameras each are configured to selectively take a picture of the welding gun.

10. The apparatus of claim 9, further comprising:

a computer that is configured to control operations of the first, second, third and fourth cameras and the measuring apparatus and to store photographing and inspection data, and a robot controller that is configured to control the robot.

11. The apparatus of claim 10, wherein the computer is configured to calculate a correction value that is based on the inspection data.

12. The apparatus of claim 11, wherein the computer is configured to transmit the inspection data and the data of the calculated correction value of the welding gun through a wireless communication to a server.

13. The apparatus of claim 12, wherein the inspection data and the calculated correction value of the welding gun are confirmed on the personal computer (PC) connected to the server.

14. The apparatus of claim 9, wherein:

the welding gun is provided as a pair vertically positioned with respect to a circumference of the frame, and the pair of welding guns are disposed in such a way that welding tips of each of the welding guns face each other, and in a state that the frame is disposed so that the welding gun is disposed where the photographing direction of the first camera crosses the photographing direction of the second camera, the first and second cameras are configured to take a picture of the welding gun.

15. The apparatus of claim 14, wherein rectilinear propagation performance and abrasion loss of the welding gun are inspected using images taken by the first and second cameras.

16. The apparatus of claim 9, wherein:

the welding gun is provided as a pair vertically positioned with respect to a circumference of the frame, and the pair of welding guns are disposed so that welding tips of each of the welding guns face each other, and in a state that the pair of welding guns are spaced apart from each other, the third camera is configured to take a picture of a welding tip of a lower positioned welding gun between the pair of welding guns, and the fourth camera is configured to take a picture of a welding tip of an upper positioned welding gun between the pair of welding guns.

17. The apparatus of claim 16, wherein the frame is disposed so that the welding gun is disposed where the photographing direction of the first camera crosses the photographing direction of the second camera.

18. The apparatus of claim 16, wherein a polishing condition of the welding gun is inspected using images taken by the third and fourth cameras.

* * * * *